(12) United States Patent
Sakamoto et al.

(10) Patent No.: US 6,892,566 B2
(45) Date of Patent: May 17, 2005

(54) GAS CONCENTRATION SENSOR

(75) Inventors: Masashi Sakamoto, Aichi (JP); Yoshikuni Sato, Aichi (JP); Hideki Ishikawa, Aichi (JP); Keigo Banno, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/393,496

(22) Filed: Mar. 21, 2003

(65) Prior Publication Data

US 2003/0209054 A1 Nov. 13, 2003

(30) Foreign Application Priority Data

May 8, 2002 (JP) .......................... 2002-133059

(51) Int. Cl.[7] .......................... G01N 29/02; G01H 5/00
(52) U.S. Cl. .......................... 73/24.01; 73/597
(58) Field of Search .......................... 73/24.01, 24.04, 73/24.05, 24.06, 861.18, 861.23, 861.25, 861.27, 861.28, 861.29, 597

(56) References Cited

U.S. PATENT DOCUMENTS 4,452,090 A * 6/1984 Kou et al. .................. 73/861.28
6,308,572 B1 * 10/2001 Ishikawa et al. ............. 73/24.01

OTHER PUBLICATIONS

SAE Technical Paper Series No. 980306, "Closed Loop Canister Purge Control System" Feb. 1998.
M. Habaguchi et al., Gasoline Vapor Concentration Sensor—On Board Management by Ultrasonic Pulse–, Proceedings for Society of Automotive Engineers of Japan 955, 1955–9. pp. 89–92. Sep. 1995.

* cited by examiner

*Primary Examiner*—Edward Lefkowitz
*Assistant Examiner*—T Miller
(74) *Attorney, Agent, or Firm*—Sughrue Mion, PLLC

(57) ABSTRACT

A gas concentration sensor includes a measurement chamber for measuring a concentration of a specific gas component in a gas under measurement; an inflow path for allowing inflow of the gas under measurement thereinto and an outflow path for allowing outflow of the gas under measurement therefrom; a reflection wall for reflecting an acoustic wave; and an acoustic wave transmitting-receiving element having a transmitting-receiving surface adapted to transmit an acoustic wave toward the reflection wall and receive an acoustic wave reflected from the reflection wall. The concentration of the specific gas in the gas under measurement is detected on the basis of a propagation time between transmission of the acoustic wave and reception of the reflected acoustic wave. When a predetermined member having the sensor attached thereto is placed in a horizontal plane, the transmitting-receiving surface faces downward. A recess is formed in a peripheral portion of the reflection wall. The recess is receded toward a back surface of the reflection wall, namely, in a direction away from the transmitting-receiving surface.

25 Claims, 7 Drawing Sheets

Fig. 1 (B) Cross Section Along X-X'

GAS CONCENTRATION SENSOR

BACKGROUND OF THE INVENTION

1. Field of the Invention

The present invention relates to a gas concentration sensor for detecting the concentration of a specific gas component of a gas under measurement on the basis of a propagation time between transmission of an acoustic wave and reception of the acoustic wave, and more particularly to a gas concentration sensor that minimizes gas concentration measurement errors and measurement inability states caused by the adhesion of standing liquid within the sensor.

2. Description of the Related Art

Conventionally, a fuel supply system for supply of fuel from a fuel tank to an engine includes a first supply system which functions in the following manner. Fuel is pumped from the fuel tank by means of a pump and then sent to an injector through a fuel pipe. The fuel supply system further includes a second supply system which functions in the following manner. Fuel vapor generated within the fuel tank is temporarily adsorbed by a canister. Accumulated fuel vapor is purged from the canister and is sent as purge gas to an intake pipe.

In an engine equipped with the first and second supply systems, in addition to fuel injected from the injector, fuel vapor, such as purge gas, (hereinafter called "fuel vapor") is supplied to a cylinder for combustion. In this combustion, control of air-fuel ratio is very important, in order to minimize the content of harmful gas, such as CO, HC (hydrocarbon), and $NO_x$, in exhaust gas, which increases with deviation of an air-fuel ratio from a theoretical ideal value. To achieve control of the air-fuel ratio, the concentration of fuel vapor is measured with high accuracy, and the amount of fuel vapor and the amount of fuel injected from the injector are controlled on the basis of the measured values. Gas concentration sensors have hitherto been used as means for detecting concentration of fuel vapor; and an example of such a conventional gas concentration sensor is an ultrasonic wave gas concentration sensor, which is currently under development. The ultrasonic wave gas concentration sensor can determine the concentration of fuel vapor on the basis of a propagation time between transmission of an acoustic wave and reception of the reflected acoustic wave.

Such an ultrasonic wave gas concentration sensor is shown in Japanese Patent Application Laid-Open (kokai) No. H7-209259. This publication proposes a structure for mounting a gas concentration sensor for a vehicle, which structure enables accurate and efficient detection of gas concentration even when liquid is produced within the sensor as a result of condensation of fuel vapor or water vapor. As shown in FIG. 10, in the proposed structure, gas holes (inflow and outflow holes 15 and 16), which allow inflow and outflow of gas in the state in which the gas concentration sensor is mounted on a vehicle or an engine, are disposed in a lowermost portion in a measurement chamber 13 provided between an ultrasonic wave transmitting-receiving element 11 for transmitting and receiving an ultrasonic wave and a reflection wall 12. Use of this structure reduces adverse effects of liquid that is generated as a result of condensation of fuel vapor and water vapor within the sensor and liquid that is generated as a result of condensation of fuel vapor and water vapor outside the sensor and enters the sensor.

However, in the case where the above-described structure is employed, there would arise a problem that liquid generated as a result of condensation of fuel vapor, water vapor, etc. is apt to adhere, for a long period of time by surface tension, to the corner between a periphery of the ultrasonic wave transmitting-receiving element 11 and a wall surface of a container 18; the corner between a peripheral portion of a reflection wall 12 and the wall surface of the container 18; and a bottom portion of the wall surface of the container 18, which surrounds the measurement chamber 13.

For example, if standing liquid 14 adheres to the ultrasonic wave transmitting-receiving element 11, the standing liquid 14 hinders transmission and reception of an ultrasonic wave, thereby lowering, for example, the output, receiving sensitivity, and transmitting-receiving efficiency of the ultrasonic wave transmitting-receiving element 11. Here, the term standing liquid refers to liquid generated as a result of condensation of fuel vapor, water vapor, etc. within or outside the sensor and standing within the sensor (within the measurement chamber) without being drained out of the sensor.

Further, when standing liquid 14 adheres to the peripheral portion of the reflection wall 12, the ultrasonic wave received by the ultrasonic wave transmitting-receiving element 11 includes not only components reflected by the reflection wall 12, but also those reflected by the surface of the standing liquid 14. As a result, the ultrasonic wave transmission distance would be a distance L2, which is shorter than a true distance L1. In this state, because the output would be calculated as if the acoustic wave velocity were increased, the gas concentration would be calculated as being lower than a true value, with the result that an accurate value of the gas concentration cannot be obtained.

In practice, in a gas concentration sensor using an ultrasonic wave, a reflection wave to be received by an ultrasonic wave element (ultrasonic wave transmitting-receiving element) is attenuated by influences attributed to the material of a sensor housing, the shape of a wall surface of a measurement chamber in which the ultrasonic wave propagates, the surface shape of a reflection wall, the propagation distance of the ultrasonic wave, the frequency of the ultrasonic wave, the gas pressure, the gas temperature, and other factors. In view of the foregoing, a technique is employed in which a threshold level is set by use of a portion of a received wave in order to change the threshold level in accordance with the amplitude of the received wave, and propagation time is measured accurately by use of the changed threshold level. However, if a portion of a received wave to be used for setting the threshold level contains an improper-path wave propagated along a path other than a proper path, the resulting threshold level would deviate from the proper value, thereby causing errors in measuring the concentration of a gas.

SUMMARY OF THE INVENTION

An object of the present invention is to provide a gas concentration sensor capable of measuring the concentration of a gas accurately and efficiently.

According to a first aspect, the present invention provides a gas concentration sensor comprising: a measurement chamber for measuring a concentration of a specific gas in gas under measurement; an inflow path for allowing inflow of the gas under measurement to the measurement chamber and an outflow path for allowing outflow of the gas under measurement from the measurement chamber; a reflection wall disposed on one end surface of the measurement chamber and adapted to reflect an acoustic wave; and an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas in the gas under measurement is detected on the basis of a propagation time between transmission of the acoustic wave and reception of the reflected acoustic wave. The sensor is characterized in that when a predetermined member having the sensor attached thereto is placed in a horizontal plane, the transmitting-receiving surface faces downward; and a peripheral portion of the reflection wall includes a recess receded toward a back surface of the reflection wall.

According to a second aspect, the present invention provides a gas concentration sensor comprising: a measurement chamber for measuring a concentration of a specific gas in gas under measurement; an inflow path for allowing inflow of the gas under measurement to the measurement chamber and an outflow path for allowing outflow of the gas under measurement from the measurement chamber; a reflection wall disposed on one end surface of the measurement chamber and adapted to reflect an acoustic wave; an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas in the gas under measurement is detected on the basis of a propagation time between transmission of the acoustic wave and reception of the reflected acoustic wave. The sensor is characterized in that when a predetermined member having the sensor attached thereto is placed in a horizontal plane, the transmitting-receiving surface assumes a horizontal posture facing downward; and a peripheral portion of the reflection wall includes a recess receded toward a back surface of the reflection wall.

According to a third aspect, the present invention provides a gas concentration sensor comprising: a measurement chamber for measuring a concentration of a specific gas in gas under measurement; an inflow path for allowing inflow of the gas under measurement to the measurement chamber and an outflow path for allowing outflow of the gas under measurement from the measurement chamber; a reflection wall disposed on one end surface of the measurement chamber and adapted to reflect an acoustic wave; and an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas in the gas under measurement is detected on the basis of a propagation time between transmission of the acoustic wave and reception of the reflected acoustic wave. The sensor is characterized in that when a predetermined member having the sensor attached thereto is placed in a horizontal plane, the transmitting-receiving surface is inclined with respect to a horizontal plane by a predetermined angle and faces downward; and a peripheral portion of the reflection wall includes a recess receded toward a back surface of the reflection wall.

Preferably, in the above-described gas concentration sensor, the outflow path or the inflow path communicate with the recess at a predetermined position lower than a front surface of the reflection wall.

Further preferably, in the above-described gas concentration sensor, the outflow path or the inflow path communicates with a region including a lowermost position of the recess.

Still further preferably, in the above-described gas concentration sensor, a bottom surface of the recess is inclined by a predetermined angle with respect to the front surface of the reflection wall.

Further preferably, in the above-described gas concentration sensor, the acoustic wave transmitting-receiving element has a second recess which is formed in a peripheral portion of the acoustic wave transmitting-receiving element and receded toward the back surface of the transmitting-receiving surface.

Further, in the above-described gas concentration sensor, the specific gas may be fuel vapor generated for use in an internal combustion engine.

BRIEF DESCRIPTION OF THE DRAWINGS

FIGS. 1(A) and 1(B) are cross-sectional views schematically showing the configuration of a gas concentration sensor according to Embodiment 1 of the present invention, wherein FIG. 1(A) is a longitudinal cross section, and FIG. 1(B) is a transverse cross section (taken along line X–X');

Figure 1:
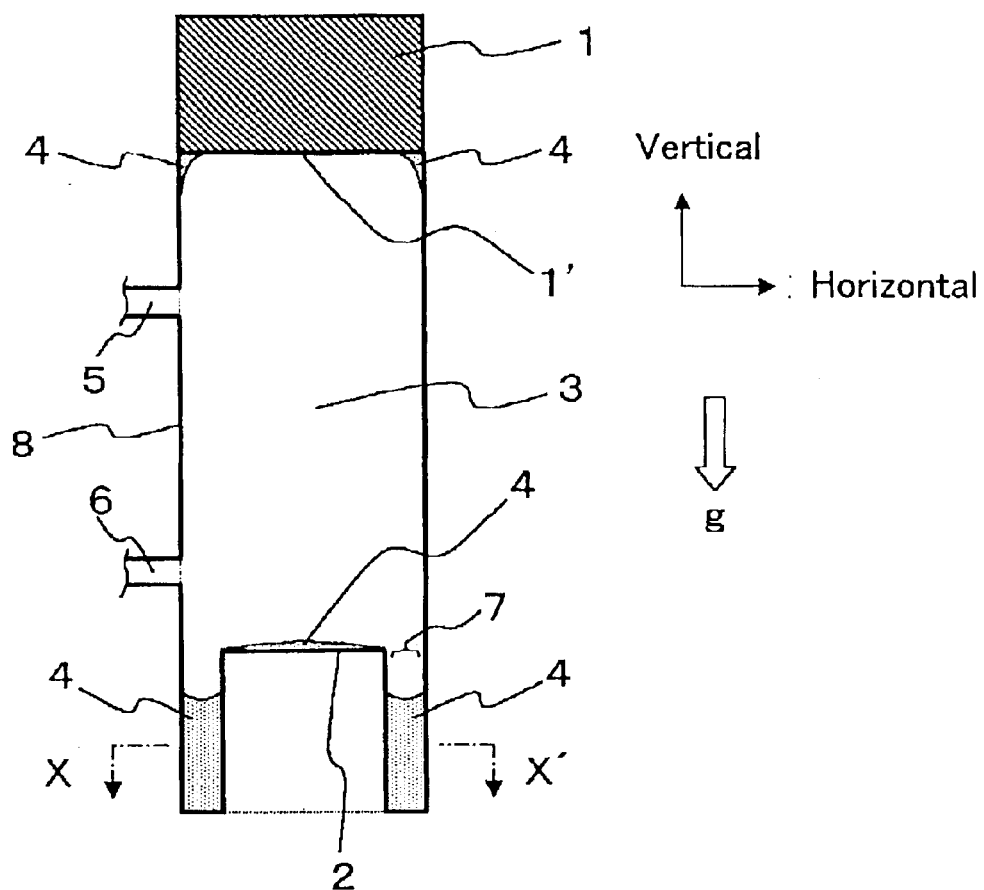
Figure 1:
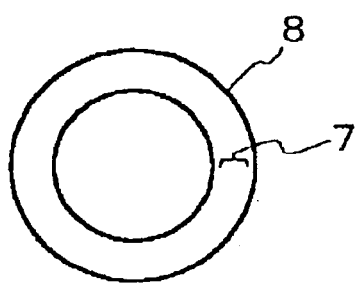

Reference numerals are used to identify items shown in the drawings as follows:
1, 11: ultrasonic wave transmitting-receiving element
1': transmitting-receiving surface
2, 12: reflection wall
3, 13: measurement chamber
4, 14: standing liquid 5, 15: inflow path
6, 16: outflow path
7: recess (reflection wall side)
7': bottom wall
8, 18: container
9: recess (ultrasonic wave transmitting-receiving element side)

DETAILED DESCRIPTION OF THE PREFERRED EMBODIMENTS

The present invention is described in detail below by reference to the drawings. However, the present invention should not be construed as being limited thereto.

A gas concentration sensor includes a measurement chamber (denoted by reference numeral 3 in FIG. 1) for measuring a concentration of a specific gas in gas under measurement; an inflow path (reference numeral 5 in FIG. 1) for allowing inflow of the gas under measurement to the measurement chamber and an outflow path (reference numeral 6 in FIG. 1) for allowing outflow of the gas under measurement from the measurement chamber; a reflection wall (reference numeral 2 in FIG. 1) disposed on one end surface of the measurement chamber and adapted to reflect an acoustic wave; and an acoustic wave transmitting-receiving element (reference numeral 1 in FIG. 1) having, on the other end surface of the measurement chamber, which surface opposes the reflection wall, a transmitting-receiving surface (reference numeral 1' in FIG. 1) adapted to transmit an acoustic wave toward the reflection wall and receive the acoustic wave reflected from the reflection wall. The concentration of the specific gas in the gas under measurement is detected on the basis of a propagation time between transmission of the acoustic wave and reception of the reflected acoustic wave. When a predetermined member having the sensor attached thereto is placed in a horizontal plane, the transmitting-receiving surface (reference numeral 1' in FIG. 1) faces downward; and a peripheral portion of the reflection wall includes a recess (reference numeral 7 in FIG. 1) receded toward a back surface of the reflection wall. This arrangement minimizes the amount of liquid which is generated as a result of condensation of fuel vapor and water vapor standing within the sensor (standing liquid; reference numeral 4 in FIG. 1) and adheres to the acoustic wave transmitting-receiving element and the reflection wall. Further, the arrangement suppresses the influences of a possible improper-path wave on the proper received wave. Therefore, possible drop in output of the acoustic wave transmitting-receiving element, possible drop in receiving sensitivity, possible measurement errors caused by variation of the acoustic wave transmission distance, and other undesirable effects can be reduced to a minimum.

Embodiment 1 of the present invention will now be described with reference to the drawings. FIG. 1 is a cross-sectional view schematically showing the configuration of a gas concentration sensor according to Embodiment 1 of the present invention, wherein FIG. 1(A) is a longitudinal cross-sectional view, and FIG. 1(B) is a cross-sectional view taken along a transverse direction (line X–X') in FIG. 1(A). Notably, standing liquid 4 does not constitute any portion of the configuration of the gas concentration sensor (the same applies to all the embodiments).

The present gas concentration sensor is a sensor for detecting the concentration of a specific gas in gas under measurement on the basis of a propagation time (sonic speed) between transmission of an acoustic wave and reception of the acoustic wave. The gas concentration sensor includes an ultrasonic wave transmitting-receiving element 1, a reflection wall 2, a measurement chamber 3, an inflow path 5, an outflow path 6, a recess 7, and a container 8. An arrow g indicates the direction of gravity.

The ultrasonic wave transmitting-receiving element 1 is disposed on an end surface (hereinafter called another surface) of the measurement chamber 3, which surface opposes the reflection wall 2. The ultrasonic wave transmitting-receiving element 1 is adapted to transmit an ultrasonic wave toward the reflection wall 2 and receive the ultrasonic wave reflected from the reflection wall 2. When the gas concentration sensor is attached to a predetermined member placed in a horizontal plane, the ultrasonic wave transmitting-receiving element 1 is attached to an upper end portion of the container 8 with its transmitting-receiving surface 1' facing downward (toward the ground), and a junction between the ultrasonic wave transmitting-receiving element 1 and the container 8 is sealed in such a manner that gas does not leak from the measurement chamber 3.

The reflection wall 2 is disposed in the vicinity of a center of a bottom of the container 8, which bottom opposes the transmitting-receiving surface 1' of the ultrasonic wave transmitting-receiving element 1 and whose inner wall surface is flat and substantially parallel to the transmitting-receiving surface 1' to reflect an ultrasonic wave transmitted from the ultrasonic transmitting-receiving element 1.

The measurement chamber 3 is a space which is surrounded by the container 8 and in which the concentration of a specific gas in gas under measurement is to be measured between the ultrasonic wave transmitting-receiving element 1 and the reflection wall 2.

The inflow path 5 is connected to the side wall of the container 8 at a position lower than the ultrasonic wave transmitting-receiving element 1 and higher than the inner wall surface of the reflection wall 2. The inflow path 5 serves as a flow passageway allowing inflow of gas under measurement to the measurement chamber 3.

The outflow path 6 is connected to the side wall of the container 8 at a position lower than the ultrasonic wave transmitting-receiving element 1 and higher than the inner wall surface of the reflection wall 2. The outflow path 6 serves as a flow passageway allowing outflow of the gas under measurement from the measurement chamber 3.

The recess 7 is a gutter-shaped portion formed in a peripheral portion of the reflection wall 2 and receded toward the back surface of the reflection wall 2, i.e., in a direction away from the transmitting-receiving element 1.

The container 8 is a generally cylindrical, tubular vessel.

According to the configuration of Embodiment 1, the gas concentration sensor is placed on a predetermined member of, for example, an engine or a vehicle in such manner that the transmitting-receiving surface 1' of the ultrasonic wave transmitting-receiving element 1 assumes a horizontal posture facing downward. Therefore, the bulk of standing liquid 4 adhering to the vicinity of a peripheral edge of the transmitting-receiving surface 1' by surface tension flows down to a lower portion of the measurement chamber 3 under the force of gravity, thereby eliminating the fear that a large amount of standing liquid 4 might stand at a peripheral portion of the ultrasonic wave transmitting-receiving element 1.

Further, because the recess 7 is provided in the peripheral portion of the reflection wall 2, the bulk of the standing liquid 4 adhering to the front surface of the reflection wall 2 flows down to the recess 7 around the reflection wall 2 under the force of gravity, thereby eliminating the fear that a large amount of standing liquid 4 might stand on the surface of the reflection wall 2.

Figure 11:
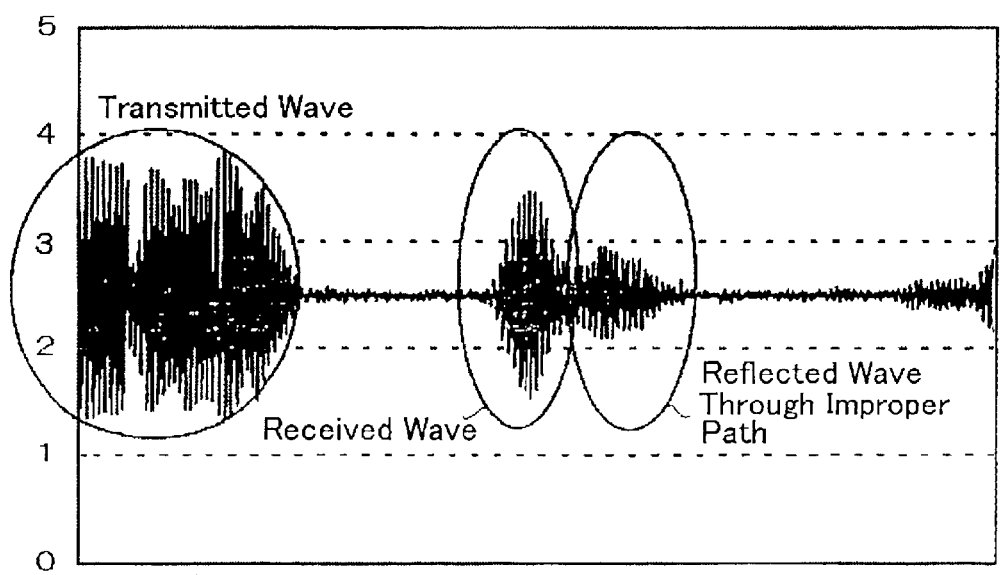
FIG. 11 is a graph showing a waveform of an ultrasonic wave when the gas concentration sensor according to Embodiment 1 of the present invention is employed.

In addition, because the recess 7 is formed in the peripheral portion of the reflection wall 2, mixing of a normally received wave (a wave reflected from the reflection wall 2) and a reflected wave propagating trough an improper path (a wave reflected from the recess 7, also called an improper-path wave) can be avoided. Therefore, the received wave and the reflected wave propagating through an improper path can be separated from each other by means of, for example, an analog switch (FIG. 11).

Figure 2:
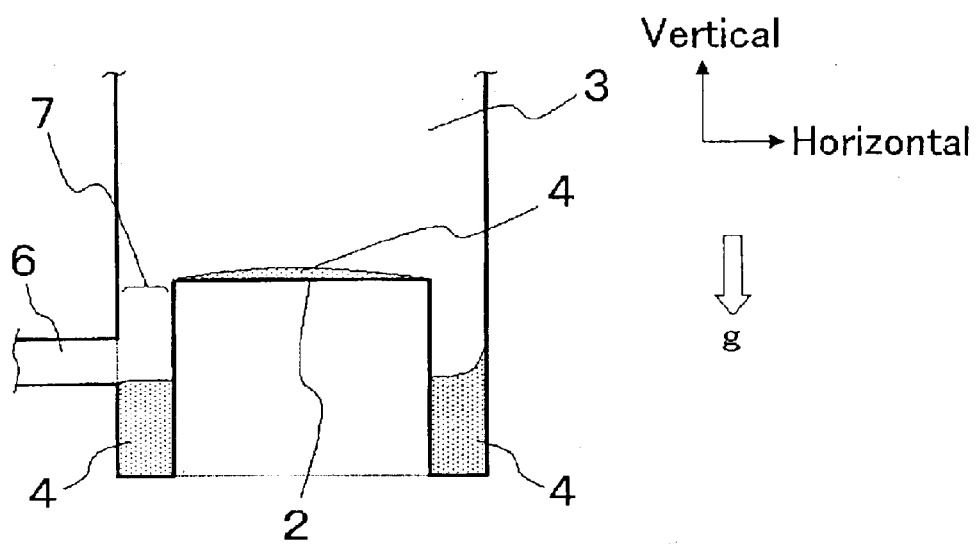
FIG. 2 is a cross-sectional view schematically showing the configuration of a bottom portion, and its vicinity, of a gas concentration sensor according to Embodiment 2 of the present invention.

Next, Embodiment 2 will be described by reference to FIG. 2. FIG. 2 is a fragmentary cross-sectional view schematically showing the configuration of a bottom portion, and its vicinity, of a gas concentration sensor according to Embodiment 2 of the present invention. An arrow g indicates the direction of gravity.

The present gas concentration sensor is identical in configuration with that of Embodiment 1, except for the position of the outflow path 6. Here, the outflow path 6 is connected to the recess 7 of the container at a position below (lower than) the front surface of the reflection wall 2.

According to Embodiment 2, because the outflow path 6 is located below the reflection wall 2, the standing liquid 4 exceeding the outflow path 6 flows into the outflow path 6 under the force of gravity even when a large amount of standing liquid 4 flows into the recess 7. As a result, the fear that standing liquid 4 might stand in an overflow state on the front surface of the reflection wall 2 is eliminated.

Figure 3:
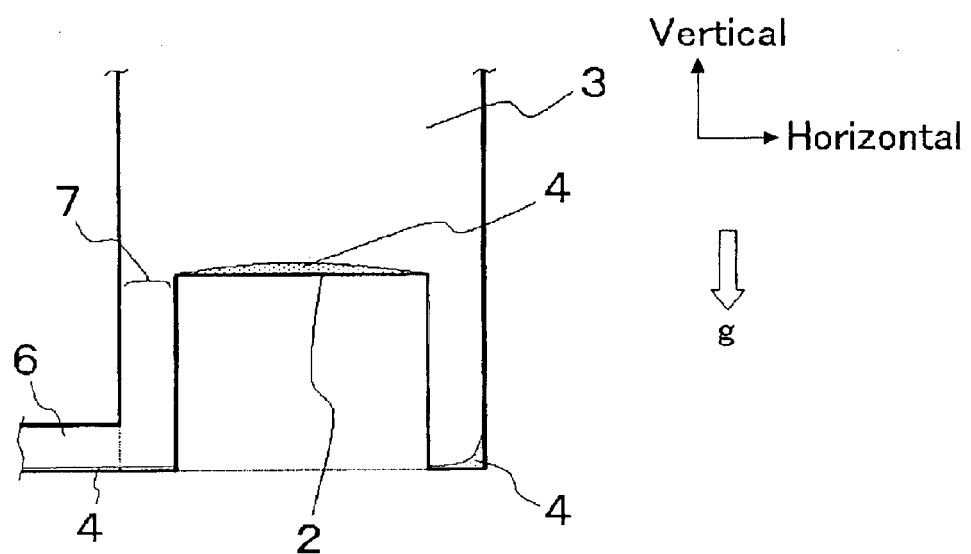
FIG. 3 is a cross-sectional view schematically showing the configuration of a bottom portion, and its vicinity, of a gas concentration sensor according to Embodiment 3 of the present invention.

Next, Embodiment 3 will be described by reference to FIG. 3. FIG. 3 is a fragmentary cross-sectional view schematically showing the configuration of a bottom portion, and its vicinity, of a gas concentration sensor according to Embodiment 3 of the present invention. An arrow g indicates the direction of gravity.

The present gas concentration sensor is identical in configuration with that of Embodiment 1, except for the position of the outflow path 6. Here, the outflow path 6 is connected to a lowermost position of the recess 7 of the container including a bottom surface of the recess 7.

According to Embodiment 3, because the outflow path 6 is located at the lowermost position of the recess 7, the bulk of the standing liquid 4 standing in the recess 7 flows into the outflow path 6 under the force of gravity, thereby eliminating the fear that a large amount of standing liquid 4 might stand within the recess 7.

Figure 4:
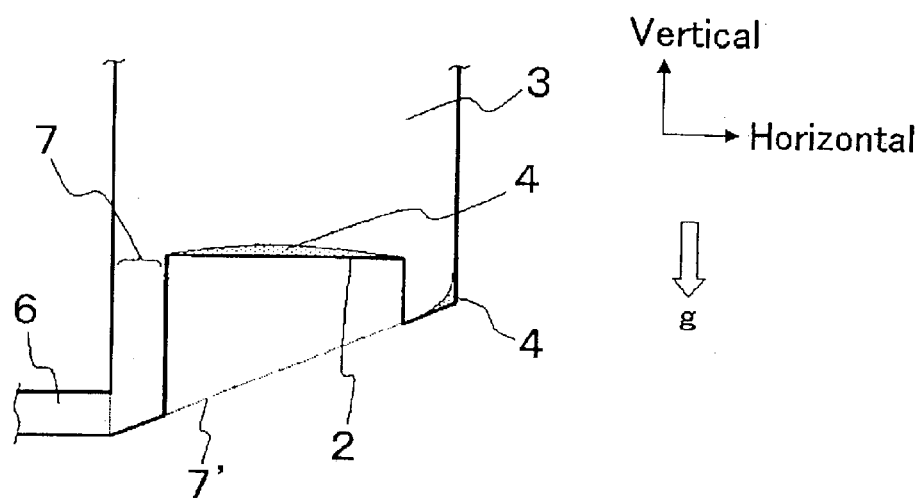
FIG. 4 is a cross-sectional view schematically showing the configuration of a bottom portion, and its vicinity, of a gas concentration sensor according to Embodiment 4 of the present invention.

Next, Embodiment 4 will now be described by reference to FIG. 4. FIG. 4 is a fragmentary cross-sectional view schematically showing the configuration of a bottom portion, and its vicinity, of a gas concentration of Embodiment 4 of the present invention. An arrow g indicates the direction of gravity.

The present gas concentration sensor is identical in configuration with that of Embodiment 1, except for the position of the outflow path 6 and the configuration of the recess 7. Here, the outflow path 6 is connected to a lowermost position of the recess 7 of the container including a bottom surface of the recess 7. Further, a bottom wall 7' of the recess 7 is not parallel to an inner wall surface of the reflection wall 2, but slants toward the outflow path 6 in the lowermost position.

According to Embodiment 4, because the bottom wall 7' of the recess 7 slants toward the outflow path 6, the bulk of the standing liquid 4 adhering to the bottom wall 7' of the recess 7 by surface tension flows and gathers to the outflow path 6 under the force of gravity, thereby eliminating the fear that a large amount of standing liquid 4 might stand in the bottom wall 7' of the recess 7.

Figure 12:
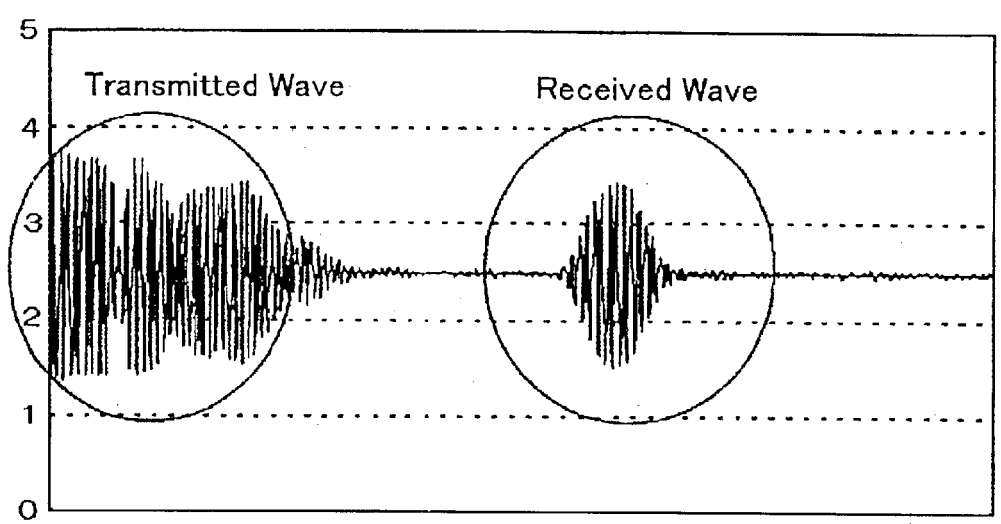
FIG. 12 is a graph showing a waveform of an ultrasonic wave when the gas concentration sensor according to Embodiment 4 of the present invention is employed.

Further, since the bottom wall 7' of the recess 7 is inclined with respect to the inner wall surface of the reflection wall 2, a wave reflected through an improper path can be attenuated by a large extent as compared with the normally received wave (or attenuated such that substantially no reflected wave reaches the ultrasonic wave transmitting-receiving element). Therefore, substantially only the normally received wave can be detected (See FIG. 12).

Figure 5:
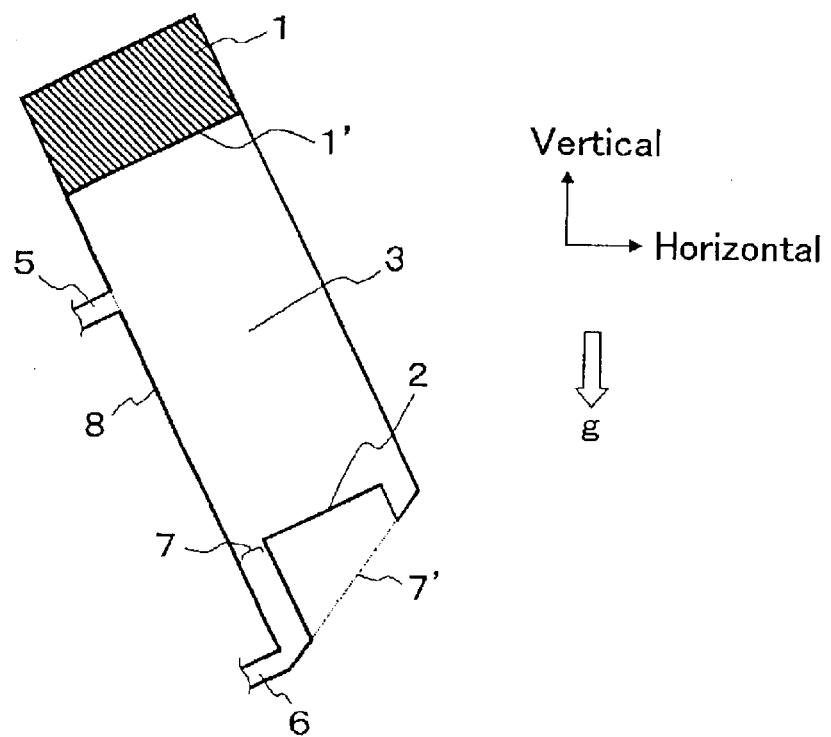
FIG. 5 is a cross-sectional view schematically showing the configuration of a gas concentration sensor according to Embodiment 5 of the present invention.
Figure 6:
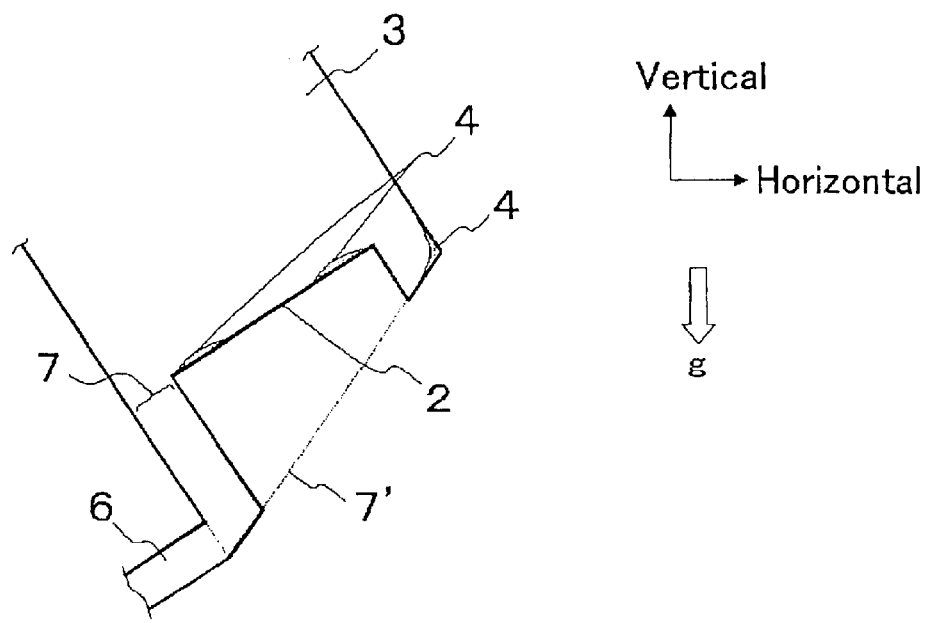
FIG. 6 is a cross-sectional view schematically showing the configuration of a bottom portion, and its vicinity, of the gas concentration sensor according to Embodiment 5 of the present invention.

Next, Embodiment 5 will now be described by reference to FIG. 5. FIG. 5 is a cross-sectional view schematically showing the configuration of a gas concentration sensor according to Embodiment 5 of the present invention. FIG. 6 is a fragmentary cross-sectional view schematically showing the configuration of a bottom portion, and its vicinity, of the gas concentration according to Embodiment 5 of the present invention. An arrow g indicates the direction of gravity.

The present gas concentration sensor is identical in configuration with that of Embodiment 4, but differs in posture from that of Embodiment 4. Here, the gas concentration sensor assumes such a posture that the outflow path 6 assumes the lowermost position to thereby incline each of the inner wall surface of the reflection wall 2 and the transmitting-receiving surface 1' of the ultrasonic wave transmitting-receiving element 1 with respect to a horizontal plane.

According to Embodiment 5, because the transmitting-receiving surface 1' of the ultrasonic wave transmitting-receiving element 1 is inclined with respect to a horizontal plane, the bulk of the standing liquid (not shown in FIG. 5) adhering to the vicinity of the periphery of the transmitting-receiving surface 1' by surface tension flows down to a lower portion of the measurement chamber 3 under the force of gravity, thereby eliminating the fear that a large amount of standing liquid might stand at the peripheral portion of the ultrasonic wave transmitting-receiving element 1.

Further, because the inner wall surface of the reflection wall 2 is inclined with respect to a horizontal plane, the bulk of the standing liquid 4 adhering to the inner wall surface of the reflection wall 2 by surface tension flows down to the recess 7 under the force of gravity, thereby eliminating the fear that a large amount of standing liquid might stand on the inner wall surface of the reflection wall 2.

Still further, because the bottom wall 7' of the recess 7 is not parallel to the reflection wall 2, the bulk of the standing liquid 4 adhering to the bottom wall 7' of the recess 7 flows down to the outflow path 6 under the force of gravity, thereby eliminating the fear that a large amount of standing liquid might stand on the bottom wall 7' of the recess 7.

In addition, because the outflow path 6 is disposed in a lowermost position of the recess 7, the bulk of the standing liquid 4 standing in the recess 7 flows down to the outflow path 6 under the force of gravity, thereby eliminating the fear that a large amount of standing liquid might stand in the recess 7.

Figure 7:
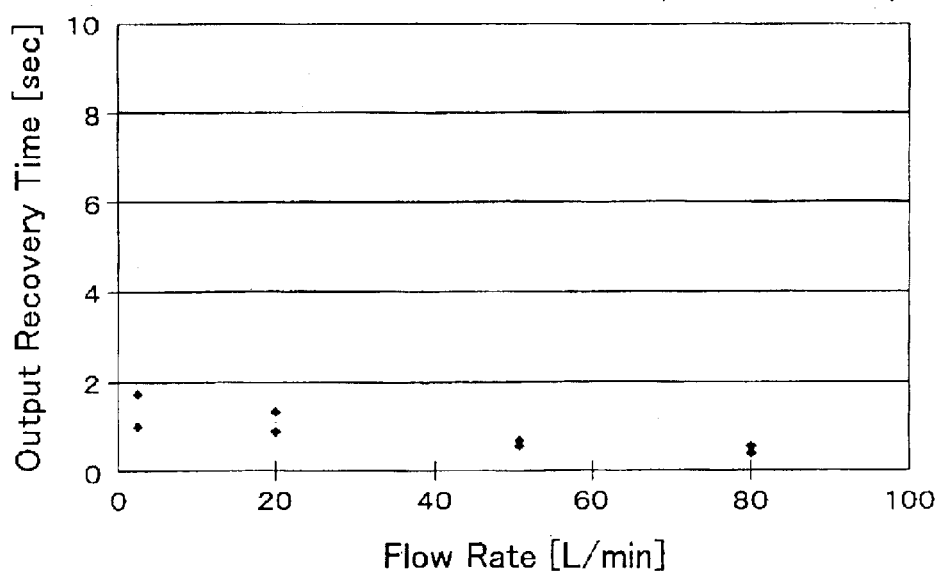
FIG. 7 is a graph showing a flow-rate dependency of output recovery time in the case of Embodiment 5 of the present invention.
Figure 8:
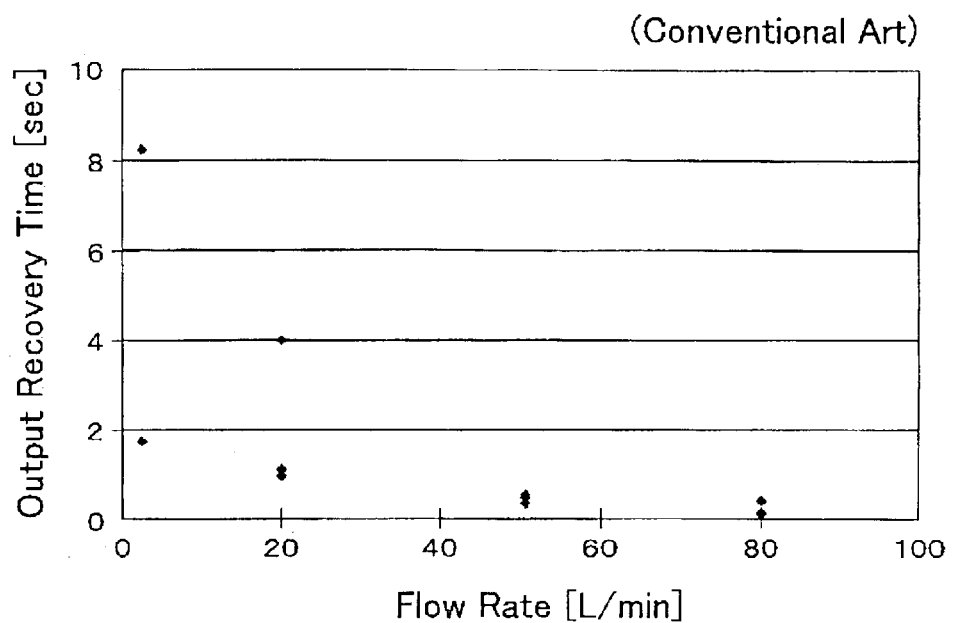
FIG. 8 is a graph showing a flow-rate dependency of output recovery time in the case of a conventional gas concentration sensor.

Next, the gas concentration sensor of Embodiment 5 and a conventional gas concentration sensor will be compared with reference to FIGS. 7 and 8. FIG. 7 is a graph showing a flow-rate dependency of output recovery time in the case of the gas concentration sensor according to Embodiment 5 of the present invention, and FIG. 8 is a graph showing a flow-rate dependency of output recovery time in the case of a conventional gas concentration sensor.

Figure 10:
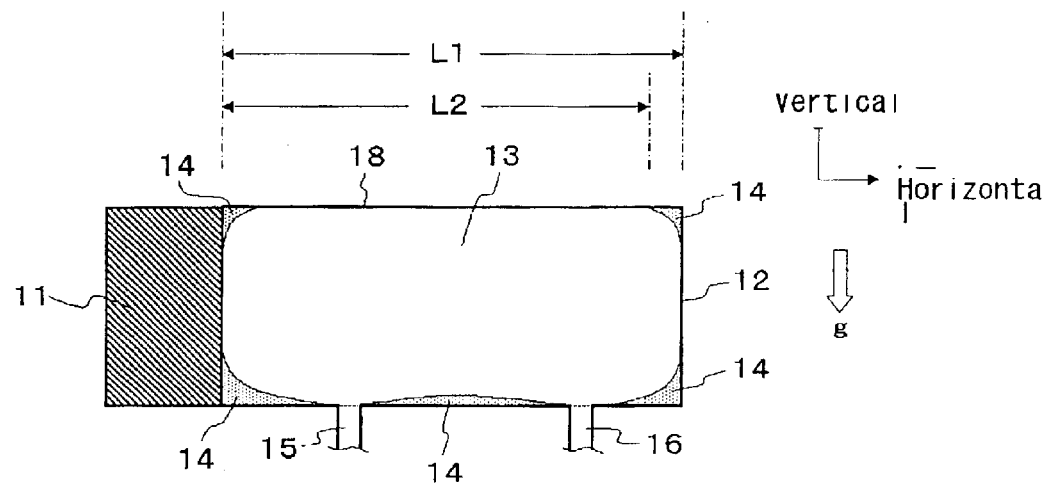
FIG. 10 is a cross-sectional view schematically showing the configuration of a conventional gas concentration sensor.

The gas concentration sensors compared here were the gas concentration sensor of Embodiment 5 shown in FIG. 5 and the conventional gas concentration sensor shown in FIG. 10. These two gas concentration sensors were identical in terms of the material of the ultrasonic wave transmitting-receiving element and that of the container, and were identical in terms of the following parameters: the diameter of the container, the distance between the transmitting-receiving surface of the ultrasonic wave transmitting-receiving element and the reflection wall, and the size of the inflow and outflow paths.

A test was performed to determine a flow-rate dependency of output recovery time for each of the gas concentration sensors. Here, the term output recovery time refers to a period of time defined as follows. First, the flow passage of the sensor is fully filled with water, and subsequently, nitrogen gas is supplied from the inflow path at a constant flow rate. A period of time from a point in time when the supply of the nitrogen gas is started and a point in time when the output level of the sensor is recovered (when the output attains the same level as that in the state where water is not present within the flow passage of the sensor) is measured as an output recovery time. FIGS. 7 and 8 each show output recovery time [sec] for each gas concentration sensor with respect to the flow of nitrogen [L/min], where [L] represents liters.

The test results for the conventional gas concentration sensor shown FIG. 8 indicate that variation of output recovery time is large, particularly on the low-flow side (lower than around 20 [L/min]) and that, in some cases, the output is not recovered even after passage of a considerably long time. At that time, the sensor was disassembled, and the surfaces of the ultrasonic wave transmitting-receiving element 11 and the reflection wall 12 were examined. This examination confirmed that a large amount of water was standing on these surfaces (See FIG. 10).

By contrast, the results for the gas concentration sensor according to Embodiment 5 shown in FIG. 7 indicate that variation in output recovery time was small across the entire range of flow rate. Further, the sensor was disassembled, and the surfaces of the ultrasonic wave transmitting-receiving element 1 and the reflection wall 2 were examined. This examined confirmed that no standing water was present (See FIG. 5).

As described above, the conventional gas concentration sensor and the gas concentration sensor of Embodiment 5 differ greatly in the amount of standing water within the container. Therefore, the gas concentration sensor of Embodiment 5, which is substantially free of standing of water, is expected to exhibit its proper performance in the case where liquid generated as a result of condensation of fuel vapor, water, etc. is apt to stand within the sensor (e.g., when the sensor is cold before startup of the engine), or in the case where water vapor, etc., is apt to condense and hence water or other liquid stands within the sensor (e.g., when the sensor cools after the engine is stopped).

Further, the gas concentration sensor of Embodiment 5 allows outflow of a sufficient amount of liquid generated as a result of condensation of fuel vapor, water, etc., even in the absence of flow of gas such as, for example, when the engine is stopped, and freezing of water, etc., within the sensor can be avoided. Therefore, the present gas concentration sensor is expected to exhibit its proper performance when employed in a motor vehicle climatized to cold regions.

Figure 9:
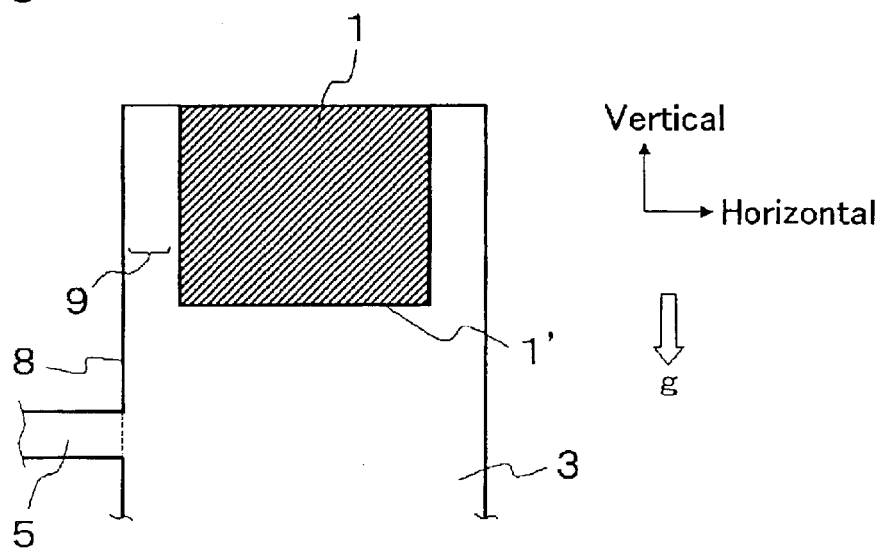
FIG. 9 is a cross-sectional view schematically showing the configuration of an ultrasonic wave transmitting-receiving element, and its vicinity, of a gas concentration sensor according to Embodiment 6 of the present invention.

Next, Embodiment 6 will be described by reference to FIG. 9. FIG. 9 is a fragmentary cross-sectional view schematically showing the configuration of an ultrasonic wave transmitting-receiving element, and its vicinity, of a gas concentration sensor according to Embodiment 6 of the present invention. An arrow g indicates the direction of gravity.

The present gas concentration sensor is identical in configuration with those of Embodiments 1 to 5, but differs in that the container 8 has, in addition to the recess formed in the peripheral portion of the reflection wall, a recess 9 receded in the peripheral portion of the ultrasonic wave transmitting-receiving element 1 toward a back surface of the transmitting-receiving surface.

According to Embodiment 6, because the peripheral portion of the ultrasonic wave transmitting-receiving element 1 also has the recess, the wall surface of the container 8 and the transmitting-receiving surface 1' of the ultrasonic wave transmitting-receiving element 1 define no angle therebetween, so that standing liquid (not shown) can hardly adhere to the peripheral portion of the transmitting-receiving surface 1'.

Notably, in the foregoing Embodiments, the acoustic wave to be transmitted and received is an ultrasonic wave. Alternatively, the acoustic wave may be an acoustic wave other than an ultrasonic wave. Further, although a single composite element serves to transmit and receive an acoustic wave, two separate elements may be provided to serve for transmission and reception of an acoustic wave, respectively. Still further, the positional relationship between the above-defined inflow path 5 and the outflow path 6 may be reversed.

According to the present invention, standing liquid within the sensor flows out promptly, and possible influence of an improper-path wave on a proper received wave can be suppressed. Therefore, the sensor is free of a drop in output of the acoustic wave transmitting-receiving element, a drop in receiving sensitivity, and a drop in transmitting-receiving efficiency; and measurement results are not accompanied by errors caused by variation of the acoustic wave transmission distance. Accordingly, concentration of a specific gas in gas under measurement can be detected accurately and efficiently.

It should further be apparent to those skilled in the art that various changes in form and detail of the invention as shown and described above may be made. It is intended that such changes be included within the spirit and scope of the claims appended hereto.

This application is based on Japanese Patent Application No. 2002-133059, filed May 8, 2002, incorporated herein by reference in its entirety.

What is claimed is:

1. A gas concentration sensor comprising:
    a measurement chamber for measuring the concentration of a specific gas component in a gas under measurement;
    an inflow path for allowing inflow of the gas under measurement to the measurement chamber and an outflow path for allowing outflow of the gas under measurement from the measurement chamber;
    a reflection wall disposed on one end surface of the measurement chamber and adapted to reflect an acoustic wave; and
    an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas component in the gas under measurement is detected on the basis of a propagation time between transmission of the acoustic wave and reception of the reflected acoustic wave, wherein the sensor is adapted such that, in use, the transmitting-receiving surface faces downward;

a peripheral portion of the reflection wall includes a recess receded away from the transmitting-receiving surface; and the outflow path or the inflow path communicates with the recess at a predetermined position lower than a front surface of the reflection wall.

2. The gas concentration sensor as claimed in claim 1, wherein the outflow path or the inflow path communicates with a region including a lowermost position of the recess.

3. The gas concentration sensor as claimed in claim 1, wherein a bottom surface of the recess is inclined by a predetermined angle with respect to the front surface of the reflection wall.

4. The gas concentration sensor as claimed in claim 1, wherein the acoustic wave transmitting-receiving element has a second recess which is formed in a peripheral portion of the acoustic wave transmitting-receiving element and receded rearwardly from the transmitting-receiving surface.

5. The gas concentration sensor as claimed in claim 1, wherein the specific gas component is fuel vapor generated for use in an internal combustion engine.

6. The gas concentration sensor as claimed in claim 1, wherein the outflow path or the inflow path is connected with the recess at a predetermined position lower than a front surface of the reflection wall.

7. The gas concentration sensor as claimed in claim 1, wherein a bottom surface of the recess is inclined by a predetermined angle with respect to the front surface of the reflection wall so as to slant towards the outflow path or the inflow path in communication with the recess.

8. A gas concentration sensor comprising:
a measurement chamber for measuring the concentration of a specific gas component in a gas under measurement;
an inflow path for allowing inflow of the gas under measurement to the measurement chamber and an outflow path for allowing outflow of the gas under measurement from the measurement chamber;
a reflection wall disposed on one end surface of the measurement chamber and adapted to reflect an acoustic wave; and
an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas component in the gas under measurement is detected on the basis of a propagation time between transmission of the acoustic wave and reception of the reflected acoustic wave,
wherein the sensor is adapted such that, in use, the transmitting-receiving surface assumes a substantially horizontal posture facing downward;
a peripheral portion of the reflection wall includes a recess receded away from the transmitting-receiving surface; and
the outflow path or the inflow oath communicates with the recess at a predetermined position lower than a front surface of the reflection wall.

9. The gas concentration sensor as claimed in claim 8, wherein the outflow path or the inflow path communicates with a region including a lowermost position of the recess.

10. The gas concentration sensor as claimed in claim 8, wherein a bottom surface of the recess is inclined by a predetermined angle with respect to the front surface of the reflection wall.

11. The gas concentration sensor as claimed in claim 8, wherein the acoustic wave transmitting-receiving element has a second recess which is formed in a peripheral portion of the acoustic wave transmitting-receiving element and receded rearwardly from the transmitting-receiving surface.

12. The gas concentration sensor as claimed in claim 8, wherein the specific gas component is fuel vapor generated for use in an internal combustion engine.

13. The gas concentration sensor as claimed in claim 8, wherein the outflow path or the inflow path is connected to the recess at a predetermined position lower than a front surface of the reflection wall.

14. The gas concentration sensor as claimed in claim 8, wherein the bottom surface of the recess is inclined by a predetermined angle with respect to the front surface of the reflection wall so as to slant towards the outflow path or the inflow path in communication with the recess.

15. A gas concentration sensor comprising:
a measurement chamber for measuring the concentration of a specific gas component in a gas under measurement;
an inflow path for allowing inflow of the gas under measurement to the measurement chamber and an outflow path for allowing outflow of the gas under measurement from the measurement chamber;
a reflection wall disposed on one end surface of the measurement chamber and adapted to reflect an acoustic wave; and
an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas component in the gas under measurement is detected on the basis of a propagation time between transmission of the acoustic wave and reception of the reflected acoustic wave,
wherein the sensor is adapted such that, in use, the transmitting-receiving surface is inclined with respect to a horizontal plane by a predetermined angle and faces downward; and
a peripheral portion of the reflection wall includes a recess receded away from the transmitting-receiving surface.

16. The gas concentration sensor as claimed in claim 15, wherein the outflow path or the inflow path communicates with the recess at a predetermined position lower than a front surface of the reflection wall.

17. The gas concentration sensor as claimed in claim 16, wherein the outflow path or the inflow path is connected with the recess at a predetermined position lower than a front surface of the reflection wall.

18. The gas concentration sensor as claimed in claim 16, wherein a bottom surface of the recess is inclined by a predetermined angle with respect to the front surface of the reflection wall so as to slant towards the outflow path or the inflow path in communication with the recess.

19. The gas concentration sensor as claimed in claim 15, wherein the outflow path or the inflow path communicates with a region including a lowermost position of the recess.

20. The gas concentration sensor as claimed in claim 15, wherein a bottom surface of the recess is inclined by a predetermined angle with respect to the front surface of the reflection wall.

21. The gas concentration sensor as claimed in claim 15, wherein the acoustic wave transmitting-receiving element has a second recess which is formed in a peripheral portion of the acoustic wave transmitting-receiving element and receded rearwardly from the transmitting-receiving surface.

22. The gas concentration sensor as claimed in claim 15, wherein the specific gas component is fuel vapor generated for use in an internal combustion engine.

23. A gas concentration sensor comprising:

a measurement chamber for measuring the concentration of a specific gas component in a gas under measurement;

an inflow path for allowing inflow of the gas under measurement to the measurement chamber and an outflow path for allowing outflow of the gas under measurement from the measurement chamber;

a reflection wall disposed on one end surface of the measurement chamber and adapted to reflect an acoustic wave; and an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas component in the gas under measurement is detected on the basis of a propagation time between transmission of the acoustic wave and reception of the reflected acoustic wave, wherein the sensor is adapted such that, in use, the transmitting-receiving surface faces downward;

a peripheral portion of the reflection wall includes a recess receded away from the transmitting-receiving surface; and wherein the acoustic wave transmitting-receiving element has a second recess which is formed in a peripheral portion of the acoustic wave transmitting-receiving element and receded rearwardly from the transmitting-receiving surface.

24. A gas concentration sensor comprising:

a measurement chamber for measuring the concentration of a specific gas component in a gas under measurement;

an inflow path for allowing inflow of the gas under measurement to the measurement chamber and an outflow path for allowing outflow of the gas under measurement from the measurement chamber;

a reflection wall disposed on one end surface of the measurement chamber and adapted to reflect an acoustic wave; and an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas component in the gas under measurement is detected on the basis of a propagation time between transmission of the acoustic wave and reception of the reflected acoustic wave, wherein the sensor is adapted such that, in use, the transmitting-receiving surface assumes a substantially horizontal posture facing downward;

a peripheral portion of the reflection wall includes a recess receded away from the transmitting-receiving surface; and wherein the acoustic wave transmitting-receiving element has a second recess which is formed in a peripheral portion of the acoustic wave transmitting-receiving element and receded rearwardly from the transmitting-receiving surface.

25. A gas concentration sensor comprising:

a measurement chamber for measuring the concentration of a specific gas component in a gas under measurement;

an inflow path for allowing inflow of the gas under measurement to the measurement chamber and an outflow path for allowing outflow of the gas under measurement from the measurement chamber;

a reflection wall disposed on one end surface of the measurement chamber and adapted to reflect an acoustic wave; and an acoustic wave transmitting-receiving element having, on the other end surface of the measurement chamber, which surface opposes the reflection wall, a transmitting-receiving surface adapted to transmit an acoustic wave toward the reflection wall and receive the acoustic wave reflected from the reflection wall, whereby the concentration of the specific gas component in the gas under measurement is detected on the basis of a propagation time between transmission of the acoustic wave and reception of the reflected acoustic wave, wherein the sensor is adapted such that, in use, the transmitting-receiving surface is inclined with respect to a horizontal plane by a predetermined angle and faces downward;

a peripheral portion of the reflection wall includes a recess receded away from the transmitting-receiving surface; and wherein the acoustic wave transmitting-receiving element has a second recess which is formed in a peripheral portion of the acoustic wave transmitting-receiving element and receded rearwardly from the transmitting-receiving surface.

* * * * *